ns Patent [19]

Hlavka

[11] 4,018,972
[45] Apr. 19, 1977

[54] ANTIBACTERIAL AGENTS CIS-BM123$\gamma_1$ AND CIS-BM123$\gamma_2$

[75] Inventor: Joseph John Hlavka, Tuxedo Park, N.Y.

[73] Assignee: American Cyanamid Company, Stamford, Conn.

[22] Filed: Mar. 8, 1976

[21] Appl. No.: 664,321

[52] U.S. Cl. ............................... 536/17; 195/31 R; 195/96; 424/181; 204/71; 536/18
[51] Int. Cl.$^2$ ........................................ C07H 15/22
[58] Field of Search ................................ 536/17, 18

[56] References Cited

UNITED STATES PATENTS 3,784,541   1/1974   Culbertson et al. .................. 536/17

*Primary Examiner*—Johnnie R. Brown
*Attorney, Agent, or Firm*—Edward A. Conroy, Jr.

[57] ABSTRACT

This disclosure describes two new antibacterial agents designated cis-BM123$\gamma_1$ and cis-BM123$\gamma_2$ produced by a novel photolytic process whereby trans-BM123$\gamma_1$ and trans-BM123$\gamma_2$ are transformed to their corresponding cis-isomers. The new antibacterial agents are active against a variety of microorganisms and thus are useful in inhibiting the growth of such bacteria wherever they may be found.

2 Claims, No Drawings

ANTIBACTERIAL AGENTS CIS-BM123γ₁ AND CIS-BM123γ₂

BRIEF SUMMARY OF THE INVENTION

This invention relates to two new antibacterial agents designated cis-BM123γ₁ and cis-BM123γ₂, to their production by photolysis, to methods for their recovery and concentration from crude solutions, and to processes for their purification. The present invention includes within its scope the antibacterial agents in dilute forms, as crude concentrates, and in pure crystalline form. The effects of the new antibacterial agents on specific microorganisms, together with their chemical and physical properties, differentiate them from previously described antibacterial agents.

Antibacterial cis-BM123γ₁ may be represented by the following structural formula (I) whereas antibacterial cis-BM123γ₂ may be represented by the following structural formula (II).

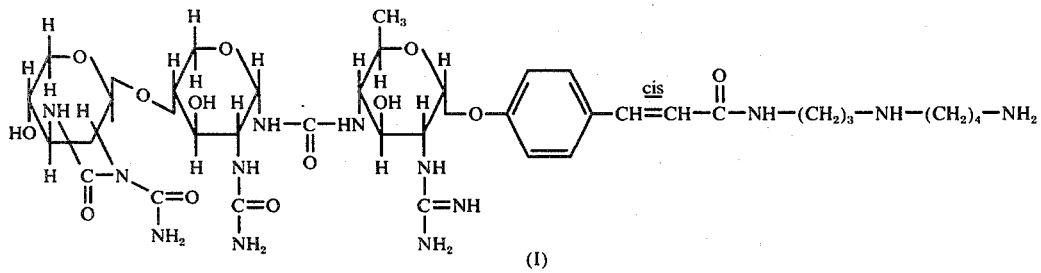

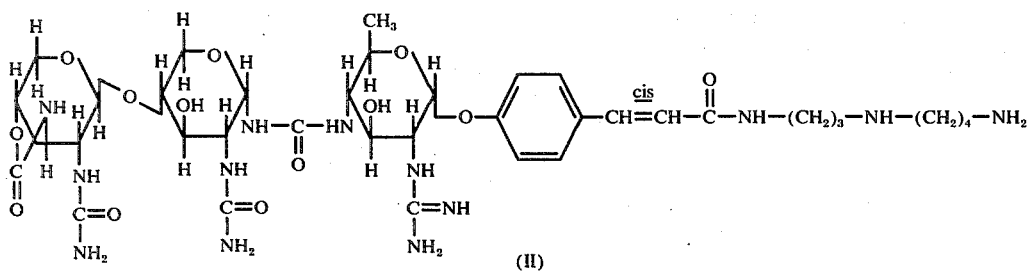

The novel antibacterial agents of the present invention are organic bases and thus are capable of forming acid-addition salts with a variety of organic and inorganic salt-forming reagents. Thus, acid-addition salts, formed by admixture of the antibacterial free base with up to three equivalents of an acid, suitably in a neutral solvent, are formed with such acids as sulfuric, phosphoric, hydrochloric, hydrobromic, sulfamic, citric, maleic, fumaric, tartaric, acetic, benzoic, gluconic, ascorbic, and related acids. The acid-addition salts of the antibacterial agents of the present invention are, in general, crystalline solids relatively soluble in water, methanol and ethanol but are relatively insoluble in non-polar organic solvents such as diethyl ether, benzene, toluene, and the like. For purposes of this invention, the antibacterial free bases are equivalent to their non-toxic acid-addition salts. Hereinafter cis-BM123γ refers to a mixture in any proportions of cis-BM123γ₁ and cis-BM123γ₂, and trans-BM123γ refers to a mixture in any proportions of trans-BM123γ₁ and trans-BM123γ₂.

DETAILED DESCRIPTION OF THE INVENTION

The new antibacterial agents which we have designated cis-BM123γ₁ and cis-BM123γ₂ are prepared by the photochemical transformation of their corresponding trans-isomers. The photolytic conversion of trans-BM123γ, trans-BM123γ₁, and trans-BM123γ₂ to the corresponding cis-BM123γ, cis-BM123γ₁, and cis-BM123γ₂ is preferably effected by dissolving or dispersing the trans-isomer starting material in water and irradiating the solution with light. The concentration of the trans-isomer starting material in the water is not critical. The light employed in the photolytic process of the present invention is advantageously of a wavelength not less than about 2,500 Angstroms and is preferably of a wavelength from about 2,500 to about 4,000 Angstroms. In order to conveniently achieve this, the reaction may be carried out in a vessel constructed of a material such as quartz, which filters out substantially all the light passing through the vessel having a wavelength below about 2,500 Angstroms. The light source is conveniently a high pressure mercury arc lamp of about 450 watts.

The temperature at which the photolysis is carried out is not particularly critical for good yields of product, but is conveniently within the range from 5° C. to 50° C.; for instance, from about 25° C. to about 30° C. The time required for substantial conversion of the trans-isomer to the corresponding cis-isomer will naturally vary with the light intensity and the temperature, and is therefore best determined by trial in the individual case. However, a period of time ranging from about 20 minutes to about 2 hours is generally sufficient.

After the irradiation step is complete, the product may be obtained by standard procedures. For example, the reaction mixture may be lyophilized or evaporated to dryness and the residue may be dissolved in a minimal amount of solvent such as ethanol or methanol. The resulting solution may be diluted with ether, and the resulting precipitated product may be recovered by filtration. Further purification may then be achieved by standard techniques such as crystallization or chromatography.

The starting materials which have been designated trans-BM123$\gamma_1$ and trans-BM123$\gamma_2$ are formed during the cultivation under controlled conditions of a new strain of an undetermined species of Nocardia. This new antibiotic producing strain was isolated from a garden soil sample collected at Oceola, Iowa and is maintained in the culture collection of the Lederle Laboratories Division, American Cyanamid Company, Pearl River, N.Y. as Culture No. BM123. A viable culture of the new microorganism has been deposited with the Culture Collection Laboratory, Northern Utilization Research and Development Division, United States Department of Agriculture, Peoria, Illinois, and has been added to its permanent collection. It is freely available to the public in this depository under its accession number NRRL 5646.

The following is a general description of the microorganism *Nocardia sp.* NRRL 5646, based on diagnostic characteristics observed. Observations were made of the cultural, physiological, and morphological features of the organism in accordance with the methods detailed by Shirling and Gottlieb, Internat. Journ. of Syst. Bacteriol. 16:313–340 (1966). The chemical composition of the culture was determined by the procedures given by Lechevalier et al., Advan. Appl. Microbiol. 14:47–72 (1971). The underscored descriptive colors and color chip designations are taken from Jacobson et al., Color Harmony Manual, 3rd edit. (1948), Container Corp. of America, Chicago, Illinois. Descriptive details are recorded in Table I through V below.

Amount of Growth

Moderate on yeast extract, asparagine dextrose, Benedict's, Bennett's, potato dextrose and Weinstein's agars; light on Hickey and Tresner's, tomato paste oatmeal and pablum agars and a trace of growth on inorganic salts-starch, Kuster's oatflake, Czapek's solution and rice agars.

Aerial Mycelium

Aerial mycelium whitish when present; produced only on yeast extract, asparagine dextrose, Benedict's, Bennett's and potato dextrose agars.

Soluble Pigments

No soluble pigments produced.

Reverse Color

Colorless to yellowish shades.

Miscellaneous Physiological Reactions

No liquefaction of gelatin; nitrates reduced to nitrates in 7 days; melanoid pigments not formed on peptone-iron agar; no peptonization or curd formation in purple milk; NaCl tolerance in yeast extract agar $\geq 4\%$ but $< 7\%$; optimal growth temperature 32° C. Carbon source utilization, according to the Pridham and Gottlieb method [J. Bacteriol. 56:107–114 (1948)] as follows: Good utilization of glycerol, salicin, d-trehalose and dextrose; fair utilization of i-inositol; and poor to non-utilization of d-tructose, maltose, adonitol, l-arabinose, lactose, d-mannitol, d-melibiose, d-raffinose, l-rhamnose, sucrose and d-xylose.

Chemical Composition

The organism belongs to cell wall type IV, i.e., contains meso-2,6-diaminopimelic acid and has a type A whole-cell sugar pattern, i.e., contains arabinose and galactose. Methylated whole cell extracts, when subjected to gas chromatography, showed fatty acid patterns similar to those produced by *Nocardia asteroides* ATCC 3308.

Micromorphology

Aerial mycelium arises from substrate mycelium as sparingly branched moderately long flexuous elements that commonly terminate in elongated primitive spirals. The flexuous elements are irregularly segmented into short elliptical to cylindrical sections (spores?) which disarticulate readily. The spiral terminal portions are less conspicuously segmented. Segments generally range 0.8–1.7 $\mu$m $\times$ 0.3–0.5 $\mu$m, averaging 0.4 $\mu$m $\times$ 1.2 um.

Diagnosis

The morphological characteristics of Culture No. BM123 are difficult to observe and interpret because of the poor development of aerial mycelium on most media. Hence, considerable importance is attached, out of necessity, to the chemical analysis in determining the generic relationship of the organism. On the basis of the system proposed by Lechevalier et al., Culture No. BM123 contains meso-2,6-diaminopimelic acid in its whole cells and sugar analysis shows arabinose and galactose to be present. Therefore, the culture belongs to cell wall type IV. A comparison of the gas chromatography pattern of Culture No. BM123 with that of *Nocardia asteroides* ATCC 3308 showed the two to be remarkably similar. Other characteristics of Culture No. BM123 that are in keeping with the Nocardia concept, are its fragmenting aerial growth on some media and the total absence of aerial growth on most media. In view of the lack of adequate criteria for the characterization of Nocardia to the species level, no attempt has been made to make this determination. Therefore, Culture No. BM123 will be considered an undetermined species of Nocardia until such a diagnosis is feasible.

TABLE I

Cultural Characteristics of Nocardia sp. NRRL 5646
Incubation: 14 days — Temperature: 32° C

| Medium | Amount of Growth | Aerial Mycelium and/or Spores | Soluble Pigment | Reverse Color | Remarks |
|---|---|---|---|---|---|
| Yeast Extract Agar | Moderate | Aerial mycelium whitish, light. | None | Mustard (3 le) | Darkened areas in substrate mycelium. Coremia formed on surface mycelium. |
| Hickey and Tresner's Agar | Light | No aerial mycelium. | None | Colorless to yellowish-green | Peripheral areas of colonies becoming olive-green. |
| Asparagine | Moderate | Trace of whitish | None | Amber | Surface lightly |

TABLE I-continued

Cultural Characteristics of Nocardia sp. NRRL 5646
Incubation: 14 days   Temperature: 32° C

| Medium | Amount of Growth | Aerial Mycelium and/or Spores | Soluble Pigment | Reverse Color | Remarks |
|---|---|---|---|---|---|
| dextrose Agar | | aerial mycelium. | | (3-lc) | wrinkled. |
| Benedict's Agar | Moderate | Aerial mycelium whitish, light. | None | Nude Tan (4 gc) | Coremia abundantly formed on surface mycelium. |
| Bennett's Agar | Moderate | Trace of whitish aerial mycelium. | None | Camel (3 ie) | Surface lightly wrinkled. |
| Inorganic Salts-starch Agar | Trace | No aerial mycelium. | None | Colorless | |
| Kuster's Oat-flake Agar | Trace | No aerial mycelium. | None | Colorless | |
| Czapek's Solution Agar | Trace | No aerial mycelium. | None | Colorless | |
| Potato dextrose Agar | Moderate | Aerial mycelium whitish, light. | None | Camel (3 ie) | |
| Tomato Paste Oatmeal Agar | Light | No aerial mycelium. | None | Colorless | |
| Pablum Agar | Light | No aerial mycelium | None | Colorless | |
| Rice Agar | Trace | No aerial mycelium. | None | Colorless | |
| Weinstein's Agar | Moderate | No aerial mycelium. | None | Colorless to yellowish | |
| Kuster's Oat-flake Agar | Trace | No aerial mycelium. | None | Colorless | |

TABLE II

Micromorphology of Nocardia sp NRRL 5646

| Medium | Aerial Mycelium and/or Sporiferous Structures |
|---|---|
| Yeast Extract Agar | Aerial mycelium arises from substrate mycelium as sparingly branched, flexuous elements that commonly terminate in elongated primitive spirals. The flexuous elements are irregularly segmented into short sections (spores?) which disarticulate readily. The spiral terminal portions are less conspicuously segmented. Segments generally range 0.8–1.7 $\mu$m × 0.3–0.5 $\mu$m, averaging 0.4 $\mu$m × 1.2 $\mu$m. |

TABLE III

Miscellaneous Physiological Reaction of Nocardia sp. NRRL 5646

| Medium | Incubation Period | Amount of Growth | Physiological Reaction |
|---|---|---|---|
| Gelatin | 7 days | Light | No liquefaction |
| Gelatin | 14 days | Good | No liquefaction |
| Organic Nitrate Broth | 7 days | Good | Nitrates reduced to nitrites |
| Organic Nitrate Broth | 14 days | Good | Nitrates reduced to nitrites |
| Peptone-iron Agar | 24–48 hours | Good | No melanin pigments produced |
| Purple Milk | 7 days | Good | No peptonization or curd formation |
| Yeast extract Agar plus (4, 7, 10 and 13%) NaCl | 7 days | Moderate | NaCl tolerance 4% but <7% |

TABLE IV

Carbon Sorce Utilization Pattern of Nocardia sp. NRRL 5646
Incubation: 10 days   Temperature: 32°C.

| Carbon Source | *Utilization |
|---|---|
| Adonitol | 0 |
| l-Arabinose | 0 |
| Glycerol | 3 |
| d-Fructose | 1 |
| i-Inositol | 2 |
| Lactose | 0 |

TABLE IV-continued

Carbon Sorce Utilization Pattern of Nocardia sp. NRRL 5646
Incubation: 10 days   Temperature: 32°C.

| Carbon Source | *Utilization |
|---|---|
| d-Mannitol | 0 |
| Salicin | 2 |
| d-Melibiose | 0 |
| d-Raffinose | 0 |
| Rhamnose | 0 |
| Maltose | 1 |
| Sucrose | 0 |
| d-Trehalose | 3 |
| d-Xylose | 0 |
| Dextrose | 3 |
| Negative Control | 0 |

*3-Good utilization
1-Poor utilization
2-Fair utilization
0-No utilization

TABLE V

Chemical Composition of Nocardia sp NRRL 5646

| Cell Wall Type | Major Constituents |
|---|---|
| Type IV | meso-DAP, arabinose, galactose |

It is to be understood that the production of the trans-isomer starting materials is not limited to this particular organism or to organisms fully answering the above growth and microscopic characteristics which are given for illustrative purposes only. In fact, it is intended to include the use of mutants produced from this organism by various means such as exposure to X-radiation, ultraviolet radiation, nitrogen mustard, actinophages, and the like. Viable cultures of such a mutant strain have been deposited with the Culture Collection Laboratory, Northern Utilization Research and Development Division, United States Department of Agriculture, Peoria, Illinois, and have been added to its permanent collection under its accession number NRRL 8050. Although the cultural, physiological, and morphological features of NRRL 8050 are substantially the same as those of NRRL 5646; NRRL 8050 varies from the parent NRRL 5646 as follows:

a. slower reduction of nitrates to nitrites; and
b. production of a rosewood tan mycelial pigment on Bennett's and yeast extract agars.

Preliminary isolation, thin layer chromatography, and paper chromatography experiments have shown that five antibiotics are produced during the aerobic fermentation of *Nocardia sp.* NRRL 5646 as heretofore designated. Nutrient media studies resulted in two types of mashes: an alpha type mash which produced primarily BM123α; and a gamma type mash which produces primarily trans-BM123$\gamma_1$ and trans-BM123$\gamma_2$ along with lesser amounts of BM123α, BM123$\beta_1$ and BM123$\beta_2$.

The antibacterial agents cis-BM123$\gamma_1$ and cis-BM123$\gamma_2$ are active in vivo against a variety of organisms. These new antibacterials are thereby potentially useful as therapeutic agents in treating bacterial infections in mammals. These new antibacterials can be expected to be usefully employed for treating or controlling bacterial infections by parenteral administration. The usefulness of these new antibacterial agents is demonstrated by their ability to control systemic lethal infections in mice. These new substances show high in vivo antibacterial activity in mice against *Escherichia coli* US311 when administered either orally or by a single subcutaneous dose to groups of Carworth Farms CF-1 mice, weight about 20 gm., infected intraperitoneally with a lethal dose of the bacteria in a $10^{-3}$ trypticase soy broth TSP dilution of a 5 hour TSP blood culture. Table VI, below, illustrates the in vivo antibacterial activity of cis-BM123γ against this bacteria.

TABLE VI

| Single Subcutaneous Dose (mg./kg. of body weight) | Alive/Total Mice Tested (7 days after infection) |
|---|---|
| 2 | 4/5 |
| 1 | 1/5 |
| 0.5 | 1/5 |
| Oral Dose (mg./kg. of body weight) | Alive/Total Mice Tested (7 days after infection) |
| 64 | 3/5 |
| Infected, non-treated controls | 18/20 Mice died within 3 days after infection |

Fermentation Process Selected to Produce Primarily BM123β and trans-BM123γ

Cultivation of *Nocardia sp.* NRRL 8050 may be carried out in a wide variety of liquid culture media. Media which are useful for the production of the antibiotics include as assimilable source of carbon such as starch, sugar, molasses, glycerol, etc.; an assimilable source of nitrogen such as protein, protein hydrolyzate, polypeptides, amino acids, corn steep liquor, etc.; and inorganic anions and cations, such as potassium, magnesium, calcium, ammonium, sulfate, carbonate, phosphate, chloride, etc. Trace elements such as boron, molybdenum, copper, etc.; are supplied as impurities of other constituents of the media. Aeration in tanks and bottles is provided by forcing sterile air through or onto the surface of the fermenting medium. Further agitation in tanks is provided by a mechanical impeller. An antifoaming agent, such as Hodag FD82 may be added as needed.

Inoculum Preparation for BM123β and trans-BM123γ

Primary shaker flask inoculum of *Nocardia sp.* NRRL 8050 is prepared by inoculating 100 milliliters of sterile liquid medium in 500 milliliter flasks with scrapings or washings of spores from an agar slant of the culture. The following medium is ordinarily used:

| | |
|---|---|
| Bacto-tryptone | 5 gm. |
| Yeast extract | 5 gm. |
| Beef extract | 3 gm. |
| Glucose | 10 gm. |
| Water to | 1000 ml. |

The flasks were incubated at a temperature from 25°–29° C., preferably 28° C. and agitated vigorously on a rotary shaker for 30 to 48 hours. The inocula are then transferred into sterile screw cap culture tubes and stored at below 0° F. This bank of vegetative inoculum is used instead of slant scrapings for inoculation of additional shaker flasks in preparation of this first stage of inoculum.

These first stage flask inocula are used to seed 12 liter batches of the same medium in 20 liter glass fermentors. The inoculum mash is aerated with sterile air while growth is continued for 30 to 48 hours.

The 12 liter batches of second stage inocula are used to seed tank fermentors containing 300 liters of the following sterile liquid medium to produce the third and final stage of inoculum:

| | |
|---|---|
| Meat solubles | 15 gm. |
| Ammonium sulfate | 3 gm. |
| Potassium phosphate, dibasic | 3 gm. |
| Calcium carbonate | 1 gm. |
| Magnesium sulfate heptahydrate | 1.5 gm. |
| Glucose | 10 gm. |
| Water to | 1000 ml. |
| The glucose is sterilized separately. | |

The third stage inoculum is aerated at 0.4 to 0.8 liters of sterile air per liter of broth per minute, and the fermenting mixture is agitated by an impeller driven at 150–300 revolutions per minute. The temperature is maintained at 25°–29° C., usually 28° C. The growth is continued for 48 to 72 hours, at which time the inoculum is used to seed a 3000 liter tank fermentaion Tank Fermentation for BM123β and trans-BM123γ

For the production of BM123β and trans-BM123γ in tank fermentors, the following fermentaion medium is preferably used:

| | |
|---|---|
| Meat solubles | 30 gm. |
| Ammonium sulfate | 6 gm. |
| Potassium phosphate, dibasic | 6 gm. |
| Calcium carbonate | 2 gm. |
| Magnesium sulfate heptahydrate | 3 gm. |
| Glucose | 20 gm. |
| Water to | 1000 ml. |
| The glucose is sterilized separately. | |

Each tank is inoculated with 5 to 10% of third stage inoculum made as described under inoculum preparation. The fermenting mash is maintained at a temperature of 25°–28° C. usually 26° C. The mash is aerated with sterile air at a rate of 0.3–0.5 liters of sterile air per liter of mash per minute and agitated by an impeller driven at 70 to 100 revolutions per minute. The fermentation is allowed to continue from 65–90 hours and the mash is harvested.

The invention will be described in greater detail in conjunction with the following specific examples.

EXAMPLE 1

Inoculum preparation for BM123$\beta$ and trans-BM123$\gamma$

A typical medium used to grow the first and second stages of inoculum was prepared according to the following formula:

| | |
|---|---|
| Bacto-tryptone | 5 gm. |
| Yeast extract | 5 gm. |
| Beef extract | 3 gm. |
| Glucose | 10 gm. |
| Water to | 1000 ml. |

Two 500 milliliter flasks each containing 100 milliliters of the above sterile medium were inoculated with 5 milliliters each of a frozen vegetative inoculum from *Nocardia sp.* NRRL 8050. The flasks were placed on a rotary shaker and agitated vigorously for 48 hours at 28° C. The resulting flask inoculum was transferred to a 5 gallon glass fermentor containing 12 liters of the above sterile medium. The mash was aerated with sterile air while growth was carried out for about 48 hours, after which the contents were used to seed a 100 gallon tank fermentor containing 300 liters of the following sterile liquid medium:

| | |
|---|---|
| Meat solubles | 15 gm. |
| Ammonium sulfate | 3 gm. |
| Potassium phosphate, dibasic | 3 gm. |
| Calcium carbonate | 1 gm. |
| Magnesium sulfate heptahydrate | 1.5 gm. |
| Glucose | 10 gm. |
| Water to | 1000 ml. |
| The glucose is sterilized separately. | |

The third stage of inoculum mash was aerated with sterile air sparged into the fermentor at 0.4 liters of air per liter of mash per minute. Agitation was supplied by a driven impeller at 240 revolutions per minute. The mash was maintained at 28° C. and Hodag FD82 was used as a defoaming agent. After 48 hours of growing time the inoculum mash was used to seed a 3000 liter fermentation.

EXAMPLE 2

Fermentation Employing *Nocardia sp.* NRRL 8050 and Medium Favoring the Production of BM123$\beta$ and trans-BM123$\gamma$ A fermentation medium was prepared according to the following formula:

| | |
|---|---|
| Meat solubles | 30 gm. |
| Ammonium sulfate | 6 gm. |
| Potassium phosphate, dibasic | 6 gm. |
| Calcium carbonate | 2 gm. |
| Magnesium sulfate heptahydrate | 3 gm. |
| Glucose | 20 gm. |
| Water to | 1000 ml. |
| The glucose is sterilized separately. | |

The fermentation medium was sterilized at 120° C. with steam at 20 pounds pressure for 60 minutes. The pH of the medium after sterilization was 6.9. Three thousand liters of sterile medium in a 4000 liter tank fermentor was inoculated with 300 liters of inoculum such as described in Example 1, and the fermentation was carried out at 26° C. using Hodag FD82 as a defoaming agent. Aeration was supplied at the rate of 0.35 liter of sterile air per liter of mash per minute. The mash was agitated by an impeller driven at 70–72 revolutions per minute. At the end of 67 hours of fermentation time the mash was harvested.

EXAMPLE 3

Isolation of BM123$\beta$ and trans-BM123$\gamma$

A 3000 liter portion of fermentation mash prepared as described in Example 2, pH 4.3, was adjusted to pH 7.0 with sodium hydroxide and filtered using 5% diatomaceous earth as a filter aid. The cake was washed with about 100 liters of water and discarded. The combined filtrate and wash was pumped upward through three parallel 8 ¼ × 48 inches stainless steel columns each containing 15 liters of CM Sephadex C-25 [Na$^+$] resin. The charged columns were washed with a total of about 390 liters of water and then developed with 200 liters of 1% aqueous solution chloride followed by 560 liters of 5% aqueous sodium chloride. The 5% aqueous sodium chloride eluate was clarified by filtration through diatomaceous earth and the clarified filtrate passed through a 9 × 60 inch glass column containing 25 liters of granular Darco activated carbon (20–40 mesh). The charged column was washed with 120 liters of water and then developed with 120 liters of 15% aqueous methanol followed by 340 liters of 50% aqueous methanol and then 120 liters of 50% aqueous acetone. The 15% aqueous methanol eluate was concentrated in vacuo to about 7 liters of an aqueous phase and the pH adjusted from 4.5 to 6.0 with Amberlite IR-45 (OH$^-$) resin (a weakly basic polystyrene-polyamine type anion exchange resin). The resin was removed by filtration and the filtrate was concentrated in vacuo to about 1 liter and then lyophilized to give 38 grams of material consisting primarily of BM123$\beta$ along with a small amount of trans-BM123$\gamma$ (primarily trans-BM123$\gamma_2$). The 50% aqueous methanol eluate was adjusted from pH 4.65 to 6.0 with Amberlite IR-45 (OH$^-$) resin. The resin was removed by filtration and the filtrate was concentrated in vacuo to about 6.3 liters and then lyophilized to give 213 grams of material consisting primarily of trans-BM123$\gamma$. The 50% aqueous acetone eluate was adjusted from pH 4.0 to 6.0 with Amberlite IR-45 (OH⁻) resin. The resin was removed by filtration and the filtrate was concentrated in vacuo to about 1.5 liters and then lyophilized to give 56 grams of impure trans-BM123γ.

EXAMPLE 4

Further Purification of trans-BM123γ

A slurry of CM Sephadex C-25 [$NH_4^+$] in 2% aqueous ammonium chloride was poured into 2.6 centimeter diameter glass column to a resin height of approximately 62 centimeters. The excess 2% aqueous ammonium chloride was drained away and a 5.0 gram sample of trans-BM123γ prepared as described in Example 5 was dissolved in about 10 milliliters of 2% aqueous ammonium chloride and applied to the column. The column was then eluted with a gradient between 6 liters each of 2% and 4% aqueous ammonium chloride. Fractions of about 75 milliliters each were collected automatically every 15 minutes. Antibiotic trans-BM123γ was located by monitoring the column effluent in the ultraviolet and by bioautography of dipped paper disks on large agar plates seeded with *Klebsiella pneumoniae* strain AD. The majority of trans-BM123γ was located between fractions 71–107 inclusive.

One hundred thirty milliliters of granular Darco activated carbon (20–40 mesh) was suspended in water, transferred to a glass column, allowed to settle and the excess water was allowed to drain away. Fractions 84–96 inclusive from the above CM Sephadex chromatography were combined and passed through the granular carbon column. The charged column was washed with 600 milliliters of water and then developed with 1 liter of 20% aqueous methanol followed by 1 liter of 50% aqueous acetone. These eluates, both of which contained trans-BM123γ, were concentrated to aqueous phases in vacuo and lyophilized to give a total of 886 milligrams of trans-BM123γ as the hydrochloride salt. A microanalytical sample was obtained by subjecting the above material to a repeat of the above process.

Antibiotic trans-BM123γ does not possess a definite melting point, but gradual decomposition starts in the vicinity of 200° C. Microanalysis of a sample equilibrated for 24 hours in a 72° F. atmosphere containing 23% relative humidity gave C, 39.44%; H, 6.10%; N, 16.19%; Cl(ionic), 11.54%; loss on drying, 8.19%. In water trans-BM123γ gave a U.V. absorption maximum at 286 nm with $E_1^{1\%}{}_{cm} = 250$. The position of this maximum did not change with pH. Trans-BM123γ had a specific rotation of $[\alpha]_D^{25°} = +71$ (C = 0.97 in water). Antibiotic trans-BM123γ exhibited characteristic absorption in the infrared region of the spectrum at the following wavelengths: 770, 830, 870, 930, 980, 1035, 1105, 1175, 1225, 1300, 1340, 1370, 1460, 1510, 1555, 1605, 1660, 1740, 2950 and 3350 cm⁻¹.

EXAMPLE 5

Isolation of trans-BM123γ₁

A slurry of CM Sephadex C-25 [Na⁺] in 2% aqueous sodium chloride was poured into a 2.6 centimeter diameter glass column to a resin height of approximately 70 centimeters. The excess 2% aqueous sodium chloride was drained away and 4.11 gram of a sample containing primarily trans-BM123γ₁ along with some trans-BM123γ₂ and other impurities, prepared as described in Example 3, was dissolved in about 10 milliliters of 2% aqueous sodium chloride and applied to the column. The column was then eluted with a gradient between 4 liters each of 2% and 4% aqueous sodium chloride. Fractions of about 75 milliliters each were collected automatically every 15 minutes. Antibiotic trans-BM123γ was located by monitoring the column effluent in the ultraviolet and by bioautography of dipped paper disks on larger agar plates seeded with *Klebsiella pneumoniae* strain AD. The majority of trans-BM123γ was located between fractions 64–90 inclusive; the initial fractions (64–80) contained a mixture of trans-BM123γ₁ and trans-BM123γ₂ whereas the later fractions (81–90) contained essentially pure trans-BM123 γ₁.

One hundred milliliters of granular Darco activated carbon (20–40 mesh) was suspended in water, transferred to a glass column, allowed to settle and the excess water was allowed to drain away. Fractions 81–90 inclusive from the above CM Sephadex chromatography were combined and passed through the granular carbon column. The charged column was washed with 500 milliliters of water and then developed with 500 milliliters of 10% aqueous methanol followed by 1 liter of 50% aqueous methanol. The 50% aqueous methanol eluate, which contained the majority of trans-BM123γ₁, was adjusted from pH 5.9 to 6.0 with Amberlite IR-45 (OH⁻¹) resin. The resin was removed by filtration and the filtrate was concentrated in vacuo to an aqueous phase and lyophilized to give 294 milligrams of white amorphous trans-BM123γ₁ as the hydrochloride salt.

Antibiotic trans-BM132γ₁ does not possess a definite melting point, but gradual decomposition starts in the vicinity of 200° C. Microanalysis of a sample equilibrated for 24 hours in a 70° F. atmosphere containing 60% relative humidity gave C, 37.84%; H, 5.73%; N, 15.58%; Cl(ionic), 10.01%; loss on drying 10.45%. In methanol trans-BM123γ₁ gave a U.V. absorption maximum at 286 nm with $E_1^{1\%}{}_{cm} = 225$. The position of this maximum did not change with pH. Trans-BM123γ₁ had a specific rotation of +55° (C=0.803 in water). Antibiotic trans-BM123γ₁ exhibited characteristic absorption in the infrared region of the spectrum at the following wavelengths: 770, 830, 870, 930, 980, 1045, 1080, 1110, 1125, 1175, 1225, 1305, 1345, 1380, 1465, 1515, 1605, 1660, 1730, 2950 and 3350 cm⁻¹.

EXAMPLE 6

Isolation of trans-BM123γ₂

A 25 gram sample containing primarily trans-BM123γ₂ and BM123β, prepared as described in Example 3, was dissolved in about 120 milliliters of 2% aqueous sodium chloride and applied to a column containing 1800 ml. of CM Sephadex C-25 [Na⁺] in 2% aqueous sodium chloride. The column was then eluted with a gradient between 20 liters each of 2% and 4% aqueous sodium chloride. The initial 12 liters of eluate was collected in a large bottle and discarded. Thereafter fractions of about 800 milliliters each were collected automatically every 40 minutes. Antibiotic trans-BM123γ was located by monitoring the column fractions in the ultraviolet. The majority of trans-BM123γ was located between fractions 7–18 inclusive; the initial fractions (7–15) contained essentially pure trans-BM123γ₂ and the later fractions (16–18) contained a mixture of trans-BM123γ₁ and trans-BM123γ₂.

Six hundred milliliters of granular Darco activated carbon (20–40 mesh) was suspended in water, transferred to a glass column, allowed to settle and the excess water was allowed to drain away. Fractions 7–15 inclusive from the above CM Sephadex chromatography were combined and passed through the granular carbon column. The charged column was washed with 3 liters of water and then developed with 3 liters of 10% aqueous methanol followed by 6 liters of 50% aqueous methanol. The 10% aqueous methanol eluate was adjusted from pH 5.8 to 6.0 with Amberlite IR 45 (OH$^-$) resin. The resin was removed by filtration and the filtrate was concentrated in vacuo to an aqueous phase and lyophilized to give 595 milligrams of white amorphous trans-BM123$\gamma_2$ as the hydrochloride salt. The 50% aqueous methanol eluate was adjusted from pH 4.6 to 6.1 with Amberlite IR 45 (OH$^-$) resin. The resin was removed by filtration and the filtrate was concentrated in vacuo to an aqueous phase and lyophilized to give 3.645 grams of slightly less pure white amorphous trans-BM123$\gamma_2$ as the hydrochloride salt.

Antibiotic trans-BM123$\gamma_2$ does not possess a definite melting point, but gradual decomposition starts in the vicinity of 200° C. Microanalysis of a sample equilibrated for 24 hours in a 70° F. atmosphere containing 60% relative humidity gave C, 36.14%; H, 5.67%; N, 15.1%; Cl(ionic), 11.11%; loss on drying 10.87%. In methanol trans-BM123$\gamma_2$ gave a U.V. absorption maximum at 286 nm with $E_{1cm}^{1\%} = 220$. The position of this maximum did not change with pH. Trans-BM123$\gamma_2$ had a specific rotation of +60° (C=0.851 in water). Antibiotic trans-BM123$\gamma_2$ exhibited characteristic absorption in the infrared region of the spectrum at the following wavelengths: 770, 830, 870, 950, 1035, 1110, 1175, 1225, 1285, 1345, 1380, 1470, 1515, 1560, 1605, 1660, 1755, 2950 and 3350 cm$^{-1}$.

EXAMPLE 7

Paper Partition and Thin Layer Chromatography of BM123$\alpha$, $\beta$ and $\gamma$ The antibacterial agents can be distinguished by paper chromatography. For this purpose Whatman No. 1 strips were spotted with a water or methanol solution of the substances and equilibrated for 1 to 2 hours in the presence of both upper and lower phases. The strips were developed overnight with the lower (organic) phase obtained from mixing 90% phenol:m-cresol:acetic acid:pyridine:water (100:25:4:4:75 by volume). The developed strips were removed from the chromatographic chamber, air dried for 1 to 2 hours, washed with ether to remove residual phenol and bioautographed on large agar plates seeded with *Klebsiella pneumoniae* strain AD. Representative Rf values are listed in Table VII below:

TABLE VII

| Component | Rf |
|---|---|
| BM123$\nu$ | 0.85 |
| BM123$\beta$ | 0.50, 0.70 |
| BM123$\alpha$ | 0.20 |

Bm123$\beta$ was composed of a major antibiotic (Rf = 0.50) called BM123$\beta_1$ and a minor antibiotic (Rf = 0.70) called BM123$\beta_2$.

The BM123 antibiotics can also be distinguished by thin layer chromatography. For this purpose precoated Cellulose F plates (0.10 milliliters thick), a form of thick layer cellulose supplied by EM Laboratories Inc., Elmsford, N.Y. were spotted with a water solution of the substance to be chromatographed (about 20–40 micrograms per spot). The plates were developed overnight with the solvent obtained by mixing 1-butanol:water:pyridine:acetic acid (15:12:10:1 by volume). The developed plates were removed from the chromatographic chamber and air dried for about 1 hour. The antibiotics were detected by using either standard ninhydrin or Sakaguchi spray reagents. Representative Rf values are listed in Table VIII below:

TABLE VIII

| Component | Rf |
|---|---|
| BM123$\nu$ | 0.17, 0.23 |
| BM123$\beta$ | 0.08, 0.14 |
| BM123$\alpha$ | 0.05 |

Both BM123$\beta$ and $\gamma$ were a mixture of two components using this system. BM123$\beta$ was composed of a major component (Rf = 0.08) which was BM123$\beta_1$ and a minor component (Rf = 0.14) which was BM123$\beta_2$. The less polar component of trans-BM123$\gamma$ (Rf = 0.23) was named trans-BM123$\gamma_1$ and the more polar component (Rf = 0.17) was named trans-BM123$\gamma_2$.

EXAMPLE 8

Preparation of cis-BM123$\gamma$

A solution of 200 mg. of trans-BM123$\gamma$ in 200 ml. of water is photolyzed with a Hanovia light in a water jacketed, three necked, round bottom flask for a period of time of half an hour, during which time the maximum U.V. absorption of the reaction solution shifts from 290 m$\mu$ to 275 m$\mu$. The reaction is best monitored by taking aliquots at various time intervals and measuring the ultraviolet absorption. The reaction is complete when the maximum absorption shifts from 290 m$\mu$ to 275 m$\mu$. The product is then recovered by lyophilization.

The above procedure is repeated but with the solution being photolyzed for 1.5 hours. Lyophilization yields 170 mg. of cis-BM123$\gamma$.

I claim:
1. A compound selected from the group consisting of antibacterial cis-BM123$\gamma_1$ of the formula:

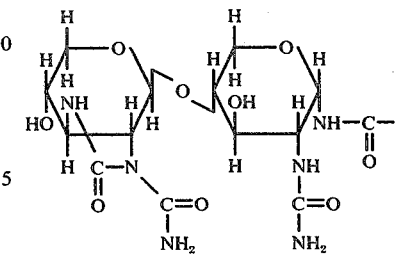

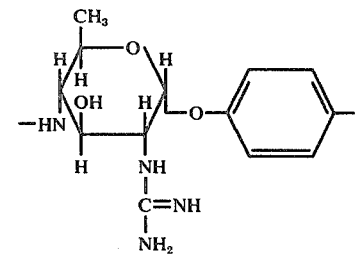

-continued
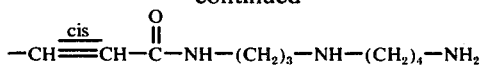
2. A compound selected from the group consisting of antibacterial cis-BM123γ$_2$ of the formula:
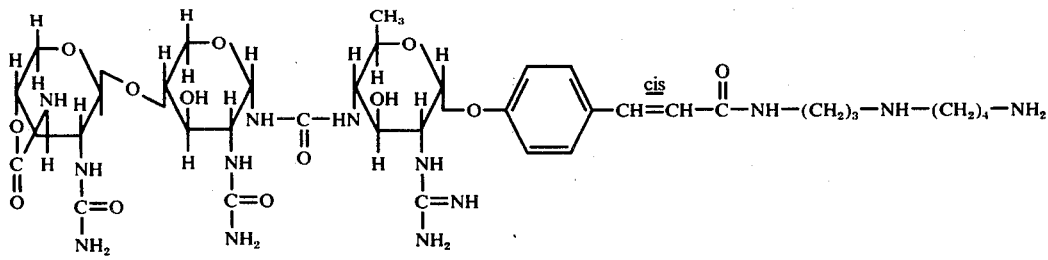
and the pharmacologically acceptable acid-addition salts thereof.